(12) United States Patent
Grader et al.

(10) Patent No.: US 9,862,171 B2
(45) Date of Patent: Jan. 9, 2018

(54) LAMINATE CHANGING DEVICE

(71) Applicant: Bayer Pharma Aktiengesellschaft, Berlin (DE)

(72) Inventors: Ludwig Grader, Andernach (DE); Roland Killer, Valley (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/518,784

(22) PCT Filed: Oct. 9, 2015

(86) PCT No.: PCT/EP2015/073327
§ 371 (c)(1),
(2) Date: Apr. 13, 2017

(87) PCT Pub. No.: WO2016/058911
PCT Pub. Date: Apr. 21, 2016

(65) Prior Publication Data
US 2017/0225442 A1    Aug. 10, 2017

(30) Foreign Application Priority Data
Oct. 14, 2014  (EP) .................................. 14188784

(51) Int. Cl.
*B32B 38/10*   (2006.01)
*B32B 37/00*   (2006.01)
(Continued)

(52) U.S. Cl.
CPC ........ *B32B 37/025* (2013.01); *A61F 13/0276* (2013.01); *A61F 13/15699* (2013.01);
(Continued)

(58) Field of Classification Search
CPC . B32B 38/10; B32B 43/006; Y10T 156/1174; Y10T 156/195; Y10T 156/1978
(Continued)

(56) References Cited

U.S. PATENT DOCUMENTS 3,522,136 A * 7/1970 McCormick ........... B31D 1/021
                                                          156/384
4,841,712 A * 6/1989 Roou ....................... B65B 9/02
                                                          156/248
(Continued)

FOREIGN PATENT DOCUMENTS

DE         4406976 C1    6/1995
DE         19837764 C1   3/2000
(Continued)

OTHER PUBLICATIONS

International Search Report dated Jan. 25, 2016 issued in corresponding PCT/EP2015/073327 application (2 pages).
English Abstract of DE 10056855 A1 published May 29, 2002.

*Primary Examiner* — Mark A Osele
*Assistant Examiner* — Nickolas Harm
(74) *Attorney, Agent, or Firm* — Millen White Zelano and Branigan, PC; Richard Traverso; Brion Heaney

(57) ABSTRACT

A device for translaminating tension-sensitive films from a first liner to a second liner, wherein the device has a first transport device, a second transport device, and a laminating device. The first transport device is configured to transport a first laminated strip to a film delaminating station. The second transport device is configured to transport a second strip-shaped liner to the laminating device, which is designed to laminate the tension-sensitive film onto the second liner in order to form a second laminated strip. The first transport device and the laminating device are arranged relative to each other such that the tension-sensitive film is (Continued)

pulled off at the film delaminating station in the direction opposite the running direction of the first laminated strip at said station.

6 Claims, 2 Drawing Sheets

(51) Int. Cl.
    *A61F 13/15*     (2006.01)
    *A61M 37/00*     (2006.01)
    *B32B 43/00*     (2006.01)
    *B32B 37/26*     (2006.01)
    *A61F 13/02*     (2006.01)

(52) U.S. Cl.
    CPC ........... *A61M 37/00* (2013.01); *B32B 43/006* (2013.01); *A61F 2013/0296* (2013.01); *A61M 2207/10* (2013.01); *B32B 38/10* (2013.01); *B32B 2037/268* (2013.01); *B32B 2535/00* (2013.01); *Y10T 156/1174* (2015.01); *Y10T 156/195* (2015.01); *Y10T 156/1978* (2015.01)

(58) Field of Classification Search
    USPC .......................................... 156/249, 715, 719
    See application file for complete search history.

(56) References Cited

U.S. PATENT DOCUMENTS

| | | | |
|---|---|---|---|
| 5,868,892 A * | 2/1999 | Klima, Jr. | B32B 38/10 |
| | | | 156/256 |
| 5,891,290 A | 4/1999 | Deurer et al. | |
| 6,649,011 B1 | 11/2003 | Hardt et al. | |
| 7,790,195 B2 | 9/2010 | Hardt et al. | |
| 2002/0124948 A1* | 9/2002 | Mikkelsen | B08B 7/0028 |
| | | | 156/247 |
| 2004/0057984 A1 | 3/2004 | Hardt et al. | |
| 2005/0211369 A1 | 9/2005 | Aso et al. | |
| 2010/0294418 A1* | 11/2010 | Yura | B32B 38/1833 |
| | | | 156/64 |
| 2012/0312462 A1* | 12/2012 | Hirata | B32B 37/0015 |
| | | | 156/235 |
| 2013/0126100 A1* | 5/2013 | Fujita | B65C 9/0006 |
| | | | 156/719 |
| 2015/0086751 A1* | 3/2015 | Robbins | H05B 6/6494 |
| | | | 428/164 |
| 2015/0183186 A1* | 7/2015 | Bigelow | B32B 7/06 |
| | | | 156/249 |

FOREIGN PATENT DOCUMENTS

| | | |
|---|---|---|
| DE | 10056855 A1 | 5/2002 |
| WO | 2013/014893 A1 | 1/2013 |

* cited by examiner

LAMINATE CHANGING DEVICE

The present invention relates in general to the transfer of a tension-sensitive film from a first strip-shaped liner to a second strip-shaped liner and in particular to the translamination of a tension-sensitive backing layer film band of a liner strip onto a strip-shaped laminate or to the translamination of a laminate composed of a tension-sensitive backing layer and an adhesive layer adhering thereto from a first liner strip to a protective film band composed of one or a plurality of strips.

The translamination of tension-sensitive films from a first strip-shaped liner to a second strip-shaped liner is important for example in the production of highly elastic transdermal therapeutic systems, which must be able to conform to any change in the shape of the skin surface they cover in order to ensure lasting full-surface skin contact during application.

Transdermal therapeutic systems (TTS), often referred to simply as TTS patches, are generally applied to the skin of a patient so that the active ingredient(s) contained in the TTS can penetrate from the transdermal therapeutic system into the skin of the patient, and thus into the blood vessels.

TTS patches generally comprise an active ingredient depot, a backing layer that is impervious to the active ingredient for covering the side of the active ingredient depot not intended to come into contact with the skin, and a protective film for covering the side of the active ingredient depot intended to come into contact with the skin. The protective film is generally attached to a surface of the active ingredient depot configured as a self-adhesive surface. The term self-adhesive is understood herein to refer to the capacity to adhere to the surface of an object on contact therewith, with it being possible to detach this adhesive bond without any substantial detrimental effect on either of the adhesion partners. In this document, therefore, the term self-adhesive is used as a synonym for the term pressure-sensitive adhesive. The protective film is used on the one hand to protect the application side from soiling and other external effects, and on the other to protect the environment, particularly other people, from possible contamination with the active ingredient(s) contained in the TTS patch. The protective film is removed before applying the system.

Two basic types of transdermal therapeutic systems are currently used, specifically matrix systems and reservoir systems. Reservoir systems contain the active ingredient(s) in a liquid, semiliquid, or solid reservoir in which the release of the active ingredient(s) is ordinarily regulated by means of a membrane. In matrix systems, the active ingredient(s) is/are embedded in a polymer matrix. Release of the active ingredient(s) is regulated by the concentration gradient of the active ingredient(s) relative to the skin.

As a rule, in order to produce transdermal therapeutic matrix systems, a self-adhesive polymer matrix containing the active ingredients is applied in web form to a liner film strip. In this document, the term web is to be understood as referring to a structure of a limited width and a length that is not further specified. A band is understood to refer to a thin, self-supporting, single or multiple-layer element of specified width but unspecified length, with the length of a band ordinarily being many times greater than its width.

The polymer matrix containing the active ingredient, also referred to as the active ingredient depot, can be narrower than the liner film strip and can also be applied to the liner film in the form of a plurality of mutually spaced webs. According to the invention, the term spaced webs refers to individual webs that are separated from one another by an intermediate space. Instead of one active ingredient, a polymer matrix can also contain a plurality of active ingredients, and it may optionally be configured in multiple layers, for example in order to control the release of the active ingredient, with different layers of the polymer matrix containing different active ingredients or active ingredient compositions and some layers optionally being free of active ingredients.

An active-ingredient impermeable backing layer strip is often applied to the upper side of the active ingredient depot facing away from the liner film, and for this purpose, said backing layer strip must be pulled off a supporting film band.

In some production methods, the liner film strip carrying an active ingredient depot does not have the properties required for a TTS protective film. The properties of a TTS protective film vary depending on the respective purpose of application or use of the TTS. For example, the protective film can be configured in overlapping form in order to counteract the discharge of a cold-flowing matrix. The use of multicomponent protective films composed of individual films of varying flexibility is also known. Embossed protective films are also in practical application. The diverse properties of liner film are determined by the production process. If the liner film cannot be used as a protective film, it must be replaced by such a protective film.

In such cases, the strip-shaped laminate composed of the active ingredient depot and the backing layer adhering thereto must be detached from the liner film and transferred onto a protective film band in order to form a TTS laminate. The protective film band may be composed of one or a plurality of strip-shaped bands. In protective film strips composed of a plurality of strip-shaped bands, the strips may be arranged either directly adjacent to or overlapping one another.

In order to isolate the transdermal therapeutic systems, areas corresponding to the TTS patches are ordinarily cut or punched out of the TTS laminate and then packaged.

In order to translaminate a material band configured as a film or laminate from one liner strip onto another, the material band must first be pulled off the liner strip and then laminated onto another liner strip. Here, the term lamination is to be understood as referring to the bonding of at least two material layers or material bands, with it being possible to achieve this bonding with or without an adhesive, for example by using heat, pressure, or a vacuum. A process for laminating a material band to another material band is referred to as translamination. A process for pulling off or detaching a translaminated material band from a liner strip is also referred to in the following as delamination.

Delamination is ordinarily carried out by separating a laminated strip into partial strips, each of which formed part of the original laminated strip. In delamination, at least one of the partial strips is diverted over a roller, a roll, or an edge (sometimes also referred to as a dispensing edge). Devices that allow the deflection of a material strip or liner strip over a so-called dispensing edge are known for example from the patent document DE 4406976 C1.

In delamination of the part to be pulled off, the other part, or both parts of a laminated strip by means of deflection by rolls, rollers, or dispensing edges, experience has shown that in order to ensure reliable separation of the laminate, the tensile forces exerted on the partial strips must be at least twice as great as the adhesive forces bonding the laminate strip layers to be separated.

If the laminate strip layer to be translaminated is a tension-sensitive film, i.e. a film that undergoes changes in shape when subjected to low tensile stresses, such tensile forces result in pronounced elongation of the film. If film elongated in this manner is applied to a second liner strip in order to form a second laminate, tensions will occur in this laminate because of the elongation.

In the use of a flexible but inelastic or only slightly elastic second strip-shaped liner, the elongation of the tension-sensitive film is frozen on application, i.e. the elongation of the film is retained in the laminate. Here, the term flexible is to be understood as referring to the property of a material of bending as a result of a force acting in a direction perpendicular to its surfaces. The tensions occurring in such laminate strips between the elongated film layer and the flexible liner layer lead to rolling up, known as the rolling effect, of transdermal therapeutic systems produced from the laminated strips, which makes them difficult to handle. If the second strip-shaped liner is also elastic, these tensions can also lead to shortening of transdermal therapeutic systems produced from this laminated strip, referred to as shrinkage, and thus to an uncertain area concentration of the active ingredients of such TTS patches. Such patches also tend to form wrinkles, making it difficult and sometimes impossible to carry out the required full-surface application of the TTS patches to the patient's skin.

The object of the present invention is therefore to provide a device that makes it possible to carry out translamination of a tension-sensitive film from a first strip-shaped liner to a second strip-shaped liner with so little elongation of the film that the second liner is not deformed by the film laminated onto it.

A corresponding device is defined by the combination of features given in claim 1. Preferred improvements of the device are subject matter of the respective dependent claims.

Embodiments of such a device for translaminating the laminate of tension-sensitive films from a first liner to a second liner have a first transport device, a second transport device, and a laminating device. Here, the first transport device is configured to transport a first laminated strip, which is composed of a first strip-shaped liner and a tension-sensitive film laminated onto said liner, from a laminate discharge device to a film delaminating station and to further transport the liner strip separated from the tension-sensitive film at the film delaminating station from the film delaminating station to a liner strip receiving device. The second transport device is further designed to transport a second strip-shaped liner to a laminating device, which is configured to translaminate a tension-sensitive film delaminated at the film delaminating station onto the second liner to form a second laminated strip and to further transport the second laminated strip from the laminating device to a laminated strip receiving device. Moreover, the first transport device and laminating device are arranged relative to each other such that the tension-sensitive film is pulled off at the film delaminating station in the direction opposite the running direction of the first laminated strip at said station.

A corresponding device minimizes the tensile forces required to detach the tension-sensitive film from the first liner, as deflection of a film causes the separating forces to be concentrated at the detaching or delaminating station.

It is to be noted that the terms "comprise," "have," "include," "contain," and "with" used in this description and the claims for listing features, as well as variations thereof, are not to be interpreted in general as an exhaustive list of features such as process steps, devices, ranges, parameters, and the like, and by no means exclude the presence of other or additional features or groups of other or additional features.

In order to prevent fluctuations in the tensile forces acting on a tension-sensitive film, preferred embodiments of the translamination devices discussed above also have a device for stabilizing the position of the film delaminating station. Suitable embodiments of such devices have at least one sensor configured to emit at least one sensor signal that is representative of the current position of the film delaminating station. In order to achieve regulated positional stabilizing of the film delaminating station, advantageous embodiments also have a controller that is configured for controlling the first transport device and the second transport device based on the sensor signal such that the position of the film delaminating station either does not change at all or does not change in a technically relevant manner relative to the first transport device and the laminating device. It should be noted in this connection that this document deviates from standard German usage in that it does not distinguish between the concepts of control and regulation. Rather, the two terms are used as synonyms, i.e. control can include the feedback of a control variable or the measured value thereof or refer to a simple control chain. This also applies to grammatical variations of these terms.

For the translamination of tension-sensitive films configured as laminates that have a pressure-sensitive adhesive layer on one side of the film, advantageous embodiments of the above-mentioned translaminating devices are configured such that the tension-sensitive film is directly guided, i.e. without touching a guide element with its self-adhesive or pressure-sensitive adhesive side, from the film delaminating station to the laminating device.

For the translamination of tension-sensitive films that do not have any pressure-sensitive adhesive surfaces, embodiments of the above-mentioned translaminating devices preferably have a detensioning device between the film delaminating station and the laminating device that is configured for tension-free guidance of the tension-sensitive film over at least part of its guidance from the film delaminating station to the laminating device.

Further features of the invention will be given in the following description of embodiments with reference to the claims and the figures. In the figures, identical or similar reference numbers will be used for functionally equivalent or similar characteristics independently of special embodiments. It is to be noted that the invention is not limited to the illustrative embodiments described, but is defined by the scope of the attached patent claims. In particular, the individual features of embodiments according to the invention can be implemented in numbers and combinations different from those implemented in the examples given below. In the following explanation of embodiments of the invention, reference is made to the attached figures, of which

Figure 1:
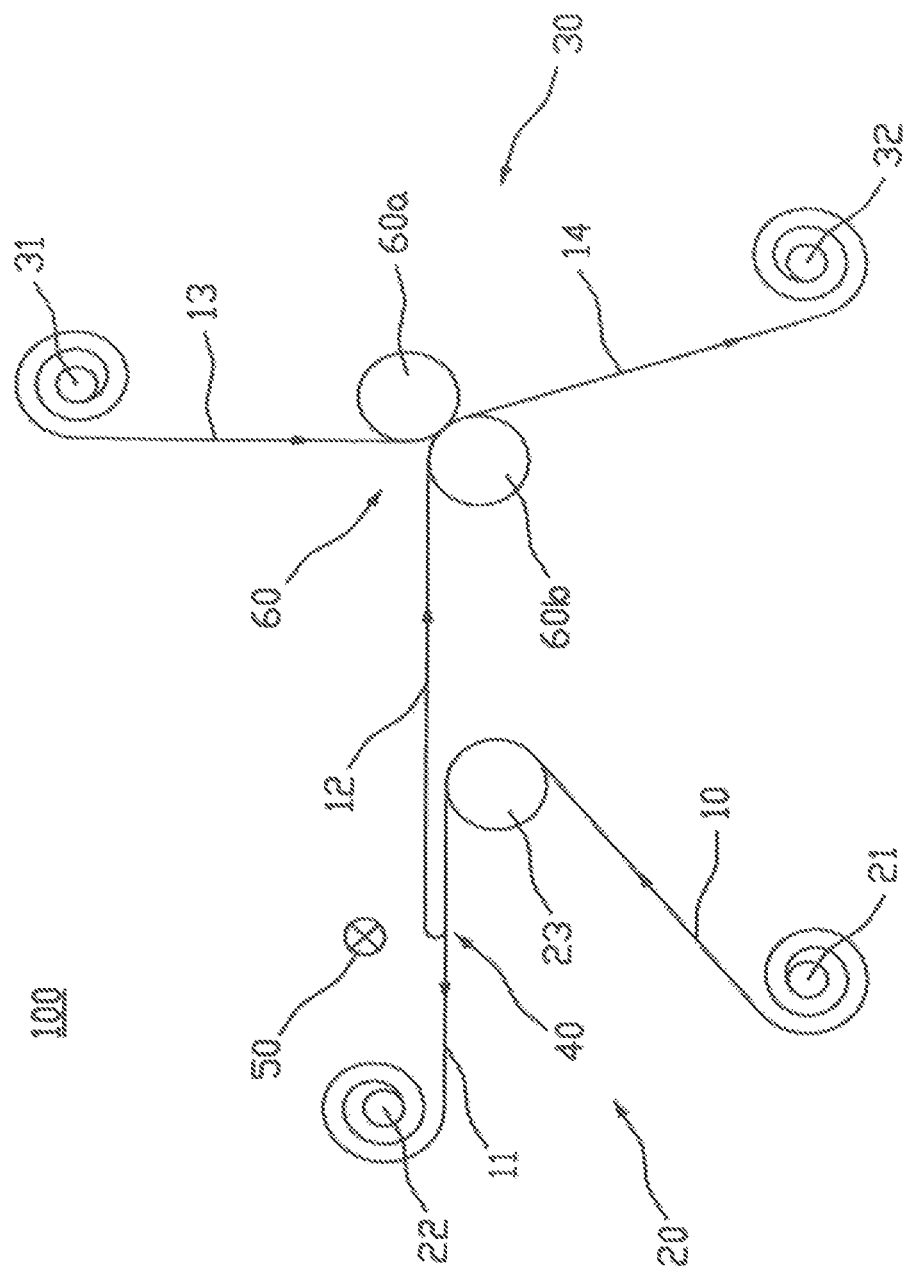
FIG. 1 shows a schematic representation of the elements of a first embodiment of a translaminating device according to the invention that are necessary for understanding.

The highly schematic illustration of FIG. 1 shows the main structure of a device 100 for translaminating the laminate or tension-sensitive film 12 from a first strip-shaped liner 11 to a second strip-shaped liner 13 according to a first illustrative embodiment.

The device 100 has a first transport device 20 and a second transport device 30. In the illustrative embodiment shown, the first transport device 20 comprises a laminate dispensing roller 21, a liner receiving roller 22, and a deflecting roller 23. The second transport device 30 comprises, in the illustrative embodiment shown, a liner dispensing roller 31, a laminate receiving roller 32, and a laminating device 60.

The laminate dispensing roller 21 of the first transport device 20 is used to dispense a laminated strip 10, wherein the laminated strip 10 is ordinarily not directly wound onto the dispensing roller 21, but is wound onto a bobbin (not shown in the figure) placed on the laminating dispensing roller 21 for unwinding the laminated strip. The laminated dispensing roller 21 is the essential component of a laminate discharge device (not shown in the figure in further detail), which may include as further components a holder and optionally a drive unit for driving the laminate dispensing roller 21.

The liner receiving roller 22 of the first transport device 20 is used to receive a first liner strip 11 obtained by separating the laminated strip 10, wherein the liner strip, like the laminated strip 10, is ordinarily not directly wound onto the roller 22, but is wound onto a bobbin (not shown in the figure) held by the liner receiving roller 22. The liner receiving roller 22 is the essential component of a liner strip receiving device (not shown in the figure in further detail), which may include as further components a holder and a drive unit for driving the liner receiving roller 22.

The deflecting roller 23 of the first transport device 20 is used for deflecting a laminated strip 10 discharged by the laminate discharge device in the direction of the delaminating station 40, at which the laminated strip 10 is separated into the tension-sensitive film 12 and the first strip-shaped liner 11. Although only one deflecting roller 23 is shown in FIG. 1, specific embodiments of the translaminating device 100 shown schematically in FIG. 1 can also have a first transport device 20 comprising a plurality of deflecting rollers 23. Other specific embodiments of the translaminating device 100 may also have a transport device 20 by means of which the laminated strip 10 of the liner strip 11 remaining after detachment of the tension-sensitive film 12 is fed from the laminate discharge device directly to the liner strip receiving device, i.e. without passing via a deflecting roller 23.

The liner dispensing roller 31 of the second transport device 30 is used for dispensing a rolled-up second liner strip 13 onto which the tension-sensitive film 12 is to be laminated. Like the laminated strip 10 on the laminate dispensing roller 21, ordinarily, the second liner strip 13 is also not wound directly onto the liner dispensing roller 31, but onto a bobbin (not shown in the figure) that is placed on the liner dispensing roller 31 for unwinding the second liner strip 13. The liner dispensing roller 31 is part of a liner discharge device (not shown in the figure in further detail), which may comprise further components such as a holder, and optionally a drive unit for the liner dispensing roller 31.

The laminate receiving roller 32 of the second transport device 30 is used to receive a second laminated strip 14, which is obtained by laminating of a tension-sensitive film 12 delaminated from a laminated strip 10 onto the second liner strip 13. Like the first liner strip 11 in the case of the liner receiving roller 22, the second laminated strip 14 is ordinarily not directly wound onto the roller 32, but is wound onto a bobbin (not shown in the figure) held by the laminate receiving roller 32. The laminate receiving roller 32 is the essential component of a laminated strip receiving device (not shown in the figure in further detail), which comprises as further components a holder and a drive unit for the laminate receiving roller 32.

In addition to transport of the tension-sensitive film 12, the second liner strip 13, and the second laminated strip 14, the laminating device 60 of the second transport device 30 is used chiefly for translaminating the tension-sensitive film 12 onto the second strip-shaped liner 13. In the embodiment shown in FIG. 1, the laminating device 60 has two rolls 60*a* and 60*b* as essential elements between which a nip is formed. In this document and in accordance with common usage, a nip is to be understood as referring to the area between two rolls in which said rolls directly or indirectly act upon each other or exert forces on each other via a medium located between them, in the present case a second liner strip 13 to which a tension-sensitive film is applied. The existence of a nip presupposes that the rolls come into contact either with each other or with a medium located between them. The second liner strip 13 is guided to the nip over a partial circumference of the first roll 60*a*, while the tension-sensitive film band 12 that is first separated from the first laminated strip is guided to the nip over a partial circumference of the second roll 60*b*. Relamination of the film 12 onto the liner 13 takes place in the nip by means of the contact pressure imparted by the pressing forces exerted by the two rolls 60*a* and 60*b* on each other.

Examples of suitable materials for the strip-shaped liner 11 or 13 include polyester, polypropylene, polyvinyl chloride, aluminum, and paper, with at least one side of the liner strip optionally having a silicone coating, polyethylene coating, fluorosilicone coating, or polytetrafluoroethylene coating. Depending on the application in question, the liner bands ordinarily have a thickness of approx. 6 to approx. 200 μm.

The tension-sensitive film 12 ordinarily has a thickness in the range of approx. 2 to approx. 15 μm and can be based on a polymer selected from the group consisting of polyolefins, olefin copolymers, polyesters, co-polyesters, polyamides, copolyamides, polyurethanes, and the like. Examples of suitable materials include polyesters, particularly polyethylene terephthalates and polycarbonates, polyolefins such as polyethylenes, polypropylenes, polybutylenes or polyisobutylenes, polyethylene oxides, polyurethanes, polystyrenes, polyamides, polyimides, polyvinyl acetates, polyvinyl chlorides, polyvinylidene chlorides, and copolymers such as acrylonitrilebutadiene-styrene terpolymers or ethylene vinyl acetate copolymers.

The tension-sensitive film 12 can also have a pressure-sensitive adhesive polymer layer that is applied to a film material as described above. The exact composition of the matrix materials depends on the respective purpose of application, for example, in the production of transdermal therapeutic systems, on the active ingredient(s) to be administered and possible further substances required for this purpose such as permeation promoters. Known examples of suitable materials for forming a polymer matrix include homo- and copolymers of (meth)acrylates, polyvinyl ethers, polyisobutylenes, polyisoprene rubber, styrene-butadiene copolymers, and styrenebutadiene-styrene copolymers. Examples of (meth)acrylate copolymers include copolymers of alkyl acrylates and/or alkyl methacrylates and further unsaturated monomers such as acrylic acid, methacrylic acid, acrylamide, dimethyl acrylamide, dimethyl aminoethyl acrylamide, acrylonitrile, and/or vinyl acetate.

In the intended use of the device 100 illustrated in FIG. 1, the laminated strip 10 discharged from the laminate discharge device is guided via a deflecting roller 23 to a film delaminating station 40. In order to illustrate this more clearly, the intended directions of operation of the individual bands are indicated in the figures by arrows. In this document, the term film delaminating station is to be understood to mean that the film band 12 is pulled off the laminated strip 10 or separated at the laminated strip 10 in order to detach the first band. The portion of the laminated strip 10 remaining after delamination of the tension-sensitive film 12, i.e. the first liner strip 11, is further guided from the film delaminating station 40 to the liner strip receiving device 22, where it is wound onto the liner receiving roller 22 or a bobbin on said roller. At the film delaminating station 40, the tension-sensitive film or the tension-sensitive film band 12 undergoes deflection at the film delaminating station 40 in a direction opposite the original running direction of the laminate 10. In the ideal case, the original and opposite direction comprise an angle of 180° so that the bending radius of the tension-sensitive film at the film delaminating station 40 is minimal.

The detachability of the tension-sensitive film 12 is determined by the separating force required to pull the film 12 off the liner 11 at the approximately linear separating site that forms at the film delaminating station 40. What is essential here is the force component oriented in a direction perpendicular to the interface between these two components of the first laminate 10 in the transition area of the detached film 12 still adhering to the liner 11. The smaller the bending radius of the film 12 at the film delaminating station 40, the greater the proportion of these force components in the entire separating force acting on the transition area. Moreover, it has been found that with small bending radii, the separating force is concentrated at the separating site, i.e. the transition area of the detached film 12 still adhering to the liner 11. As the separating force is generated by the tensile force exerted on the tension-sensitive film 12, it is thus possible to separate the first laminated strip 10 with low tensile forces, resulting in less elongation of the film band 12.

As illustrated in FIG. 1, in order to ensure that the small bending radii required for this purpose are provided, the film 12 is pulled off in the form of a free loop, i.e. without using a deflecting roller or a dispensing edge at the film delaminating station 40. Even when the conversion of the tensile force exerted on the film 12 to an effective separating force is at a maximum on deflection of the film 12 at the free loop, with the change in direction of the tension-sensitive film being 180°, the separating force decreases only minimally under the same tensile forces if the deflection of the film band at the delaminating station 40 is only approx. 150°. The change in direction of the film at the delaminating station should therefore advantageously be in the range of 150° to 180°, and the change in direction, for example when the film delaminating station 40 is arranged directly on the deflecting roller 23, can also be somewhat more than 180°.

In order to make detachment of the tension-sensitive film band 12 from the liner strip 11 as even as possible and keep fluctuations in the tensile forces acting on the film 12 as low as possible, the first and second transport devices should preferably be controlled as a function of the position of the film delaminating station 40, specifically such that the position of the film delaminating station remains practically unchanged, i.e. with the range of control accuracy. In order to ensure such a stationary position of the film delaminating station 40, a sensor 50 that determines the position of the free loop is used. As the bending radius of the free loop formed when the film 12 is pulled off is very small, any device can be used as sensor that makes it possible to determine the position of one edge. Examples of suitable sensors therefore include sensor systems based on light scattering and image-processing devices, in which other sensor systems can also be used, for example those based on the difference in reflection behavior between the pulled-off film side and the exposed liner strip side. The sensor 50 or the sensor system 50 preferably emits a sensor signal whose value is representative of the respective current position of the film delaminating station 40 and is used by the control unit for stabilizing the stationary position of the film delaminating station 40 (not shown in the figures).

The stationary position of the film delaminating station 40 is essentially controlled by coordinating the transport speeds of the first laminate 10 and second laminate 14, as this determines the tensile forces exerted on the film band 12 delaminated from the first laminated strip 10. In embodiments of the device 100, for this purpose, only the liner receiving roller 11 and the laminate receiving roller 32 are actively driven. The laminate and liner dispensing rollers 21 or 31 respectively are passively driven via the laminated strip 10 or the liner strip 13. This also applies to embodiments of the deflecting roller 23 and the two rolls 60a and 60b of the laminating device 60. In other embodiments of a translaminating device 100, positional control of the film delaminating station 40 is carried out by coordinating the drive units of the liner receiving roller 22 and the laminating device 60, with only one of the two rolls 60a or 60b being actively driven as a rule. Coordination of the drive units again takes place depending on the respective current position of the free loop determined by the sensor 50 or on the speed of positional change of the loop, i.e. based on a corresponding sensor signal as a control variable.

Pulling the tension-sensitive film 12 off in the above-described free loop minimizes the tensile forces acting on the film while it is being pulled off. Positional control of the film delaminating station 40 also ensures that the separating forces resulting from the tensile forces are constantly adapted to the respective current adhesive strength or adhesive forces, making it unnecessary to apply tensile forces to the film band as safety reserves.

The translaminating device 100 illustrated in FIG. 1 is particularly well suited for tension-sensitive film bands 12 composed of a thin tension-sensitive plastic strip which is coated on the side facing toward the liner strip 11 with a pressure-sensitive adhesive layer, for example a self-adhesive polymer layer containing an active ingredient. Of course, the device 100 is also suitable for translaminating the laminate of film bands 40 that adhere directly to the liner strip 11 without an adhesive, for example by means of prior translamination under pressure and/or at elevated temperatures.

Figure 2:
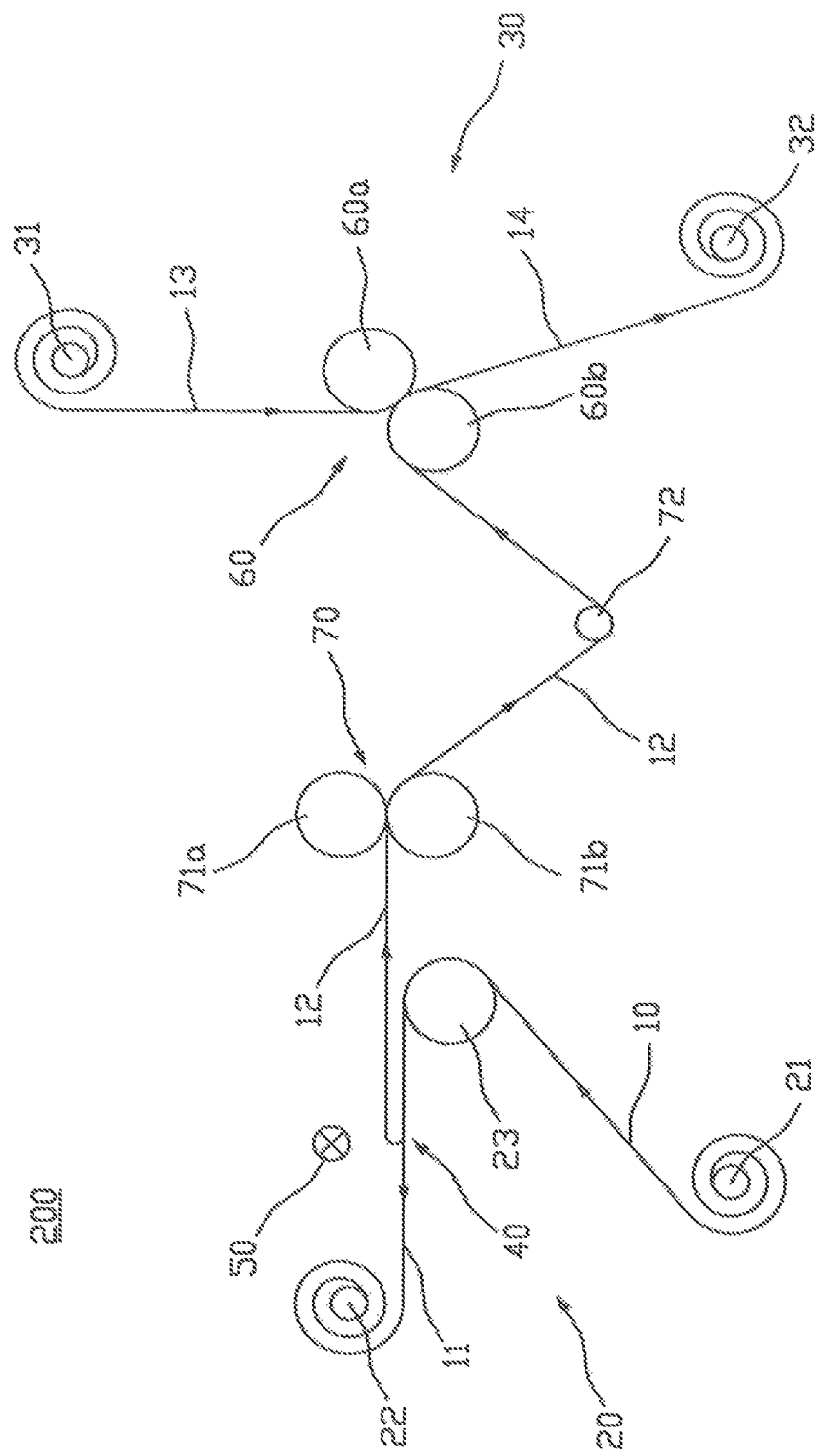
FIG. 2 shows a schematic representation of the elements of a second embodiment of a translaminating device according to the invention that are necessary for understanding.

In contrast to the translaminating device 100 according to FIG. 1, the translaminating device 200 shown in FIG. 2 has a detensioning device 70 arranged between the film delaminating station 40 and the laminating device 60. By means of the detensioning device 70, any elongation of the tension-sensitive film 12 can be reversed or at least reduced to an unharmful level. As the other components of the translaminating device 200 correspond to those of the translaminating device 100, only the detensioning device 70 will be discussed below, and the reader is referred to the above explanations with respect to other components.

The detensioning device illustrated in FIG. 2 has a drive unit 71 comprising the rolls 71a and 71b and a so-called dancer roll 72. As in the above-described translaminating device 100, the first laminated strip 10 is optionally first guided to the film laminating station 40 via an optional deflecting roller 23. For detachment, the tension-sensitive film band 12 deflected in a free loop at the film delaminating station 40 opposite to the original transport direction of the laminated strip 10 is guided through the nip formed between the two drive rolls 71a and 71b, in which the tensile forces required for detachment are exerted on the film band 12.

In contrast to the translaminating device 100 according to FIG. 1, the stationary position of the film delaminating station 40 in a translaminating device 200 as shown in FIG. 2 is preferably controlled by a controller of the first transport device 20 and drive unit 71. In particular, this control involves coordination of the transport speeds of a first laminate 10 and the delaminated film band 12 such that the position of the free loop remains stationary within the range of control accuracy.

The roll pair drive unit 71 illustrated in FIG. 2 is particularly well suited for the delamination of tension-sensitive films that do not have a pressure-sensitive adhesive surface. Instead of the roll pair, alternative embodiments of the translaminating device 200 have a drive unit based on a vacuum suction roll or a vacuum suction strip that comes into contact with the film band on its non-adhesive surface in order to transport said film band.

After the drive unit 71, the film band 12 passes through a stabilizing section in which no or minimal tensile forces are exerted on the film 12, making it possible to reverse elongation of the film. In order to form the stabilizing section of the detensioning device 70, the film band 12 is preferably guided between the drive unit 71 and laminating device 60 in such a way that it sags. This sagging can optionally be stabilized, as shown in FIG. 2, by means of a dancer roll 72, i.e. a lightweight roll that is loosely placed on the sagging film 12. In embodiments of the translaminating device 200, the position of the dancer roll 72 (or the sagging portion of the film band if it is allowed to sag freely) can be monitored by means of one or a plurality of sensors (not shown in the figure), and the speed of the laminating device 60 can be controlled independently of the signals received from these sensors in such a way that a stationary position of the dancer roll 72 (or the sagging portion of the film) is achieved.

The translaminating device 200 shown in FIG. 2 is particularly well suited for translaminating the laminate of film bands 12 that undergo intolerable elongation on detachment from the first liner strip 11.

The invention claimed is:

1. A device for translaminating tension-sensitive films (12) from a first liner (11) to a second liner (13), wherein the device (100, 200) has a first transport device (20), a second transport device (30), and a laminating device (60) and wherein the first transport device (20) is configured to transport a first laminated strip (10), which is composed of a first strip-shaped liner (11) and a tension-sensitive film (12) laminated onto said liner, from a laminate discharge device to a film delaminating station (40) and to further transport the liner strip (11) separated at the film delaminating station (40) from the tension-sensitive film (12) to a liner strip receiving device, the second transport device (30) is configured to transport a second strip-shaped liner (13) to the laminating device (60), which is configured to laminate the tension-sensitive film (12) at the film delaminating station (40) onto the second liner (13) in order to form a second laminated strip (14) and to further transport the second laminated strip from the laminating device (60) to a laminated strip receiving device, and the first transport device (20) and the laminating device (60) are arranged relative to each other such that the tension-sensitive film (12) is pulled off at the film delaminating station (40) in the direction opposite the running direction of the first laminated strip (10) at said station.

2. The device as claimed in claim 1, further comprising a device for stabilizing the position of the film delaminating station.

3. The device as claimed in claim 2, wherein the device for stabilizing the position of the film delaminating station has at least one sensor configured to emit at least one sensor signal that is representative of a current position of the film delaminating station.

4. The device as claimed in claim 3, further having a controller, which is configured for controlling the first transport device and second transport device based on the sensor signal such that the position of the film delaminating station does not change relative to the first transport device and the laminating device.

5. The device as claimed in claim 1, which is configured for directly guiding the delaminated tension-sensitive film from the film delaminating station to the laminating device.

6. The device as claimed in claim 1, which further has a detensioning device that is configured for tension-free guidance of the tension-sensitive film over at least part of its guidance between the film delaminating station and the laminating device.

* * * * *